(12) United States Patent
Kao et al.

(10) Patent No.: US 6,852,659 B1
(45) Date of Patent: Feb. 8, 2005

(54) METHOD FOR PREPARING A CATALYST COMPOSITION AND ITS USE IN A POLYMERIZATION PROCESS

(75) Inventors: Sun-Chueh Kao, Belle Mead, NJ (US); Parul A. Khokhani, Manalapan, NJ (US)

(73) Assignee: Univation Technologies, LLC, Houston, TX (US)

(*) Notice: Subject to any disclaimer, the term of this patent is extended or adjusted under 35 U.S.C. 154(b) by 888 days.

(21) Appl. No.: 09/714,477

(22) Filed: Nov. 16, 2000

(51) Int. Cl.[7] .............................. B01J 31/38; C08F 4/44
(52) U.S. Cl. ..................... 502/104; 502/152; 502/155; 526/161; 526/171
(58) Field of Search ................................ 526/161, 171; 502/104, 152, 155

(56) References Cited

U.S. PATENT DOCUMENTS 5,834,393 A * 11/1998 Jacobsen et al. ............ 502/152

FOREIGN PATENT DOCUMENTS

| | | |
|---|---|---|
| EP | 0 819 706 A1 | 1/1998 |
| EP | 0 890 581 A1 | 1/1999 |
| EP | 0 893 454 A1 | 1/1999 |
| WO | WO 94/07928 A1 | 4/1994 |
| WO | WO 95/14044 A1 | 5/1995 |
| WO | WO 96/23010 A1 | 8/1996 |
| WO | WO 96/27439 A1 | 9/1996 |
| WO | 0 890 581 A1 * | 1/1999 |
| WO | WO 99/12981 A1 | 3/1999 |
| WO | WO 00/05237 A1 | 2/2000 |

* cited by examiner

*Primary Examiner*—Robert D. Harlan
(74) *Attorney, Agent, or Firm*—Jaimes Sher; Kevin M. Faulkner

(57) ABSTRACT

The present invention relates to a catalyst composition of a supported activator, a catalyst compound and an ionizing activator and its use in a process for polymerizing olefin(s). The invention is also directed to a method for making the catalyst composition above.

8 Claims, No Drawings

METHOD FOR PREPARING A CATALYST COMPOSITION AND ITS USE IN A POLYMERIZATION PROCESS

FIELD OF THE INVENTION

The present invention relates to a method for preparing a catalyst composition and for its use in a process for polymerizing olefin(s). In particular, the invention is directed to a method for preparing a catalyst composition of a supported activator and a catalyst compound and ionizing activator. More specifically, the invention is directed to a catalyst composition of a supported activator, a Group 15 containing transition metal catalyst compound and a Group 13 containing ionizing activator.

BACKGROUND OF THE INVENTION

Advances in polymerization and catalysis have resulted in the capability to produce many new polymers having improved physical and chemical properties useful in a wide variety of superior products and applications. With the development of new catalysts the choice of polymerization-type (solution, slurry, high pressure or gas phase) for producing a particular polymer has greatly expanded. Also, advances in polymerization technology have provided more efficient, highly productive and economically enhanced processes. Especially illustrative of these advances is the development of technology utilizing bulky ligand metallocene catalyst systems. In particular, in a slurry or gas phase process where typically a supported catalyst system is used, there are a variety of different methods described in the art for supporting bulky ligand metallocene catalyst systems.

More recently, developments have lead to the discovery of anionic, multidentate heteroatom ligands as discussed by the following articles: (1) Kempe et al., "Aminopyridinato Ligands—New Directions and Limitations", $80^{th}$ Canadian Society for Chemistry Meeting, Windsor, Ontario, Canada, Jun. 1–4, 1997; (2) Kempe et al., *Inorg. Chem.* 1996 vol 35 6742; (3) Jordan et al. of polyolefin catalysts based on hydroxyquinolines (Bei, X.; Swenson, D. C.; Jordan, R. F., *Organometallics* 1997, 16, 3282); (4) Horton, et. al., "Cationic Alkylzirconium Complexes Based on a Tridentate Diamide Ligand: New Alkene Polymerization Catalysts", Organometallics, 1996, 15, 2672–2674 relates to tridentate zirconium complexes; (5) Baumann, et al., "Synthesis of Titanium and Zirconium Complexes that Contain the Tridentate Diamido Ligand [((t-Bu-d$_6$)N—O—C$_6$H$_4$)$_2$O]$^{2-}$ {[NON}$^{2-}$) and the Living Polymerization of 1-Hexene by Activated [NON]ZrMe2", Journal of the American Chemical Society, Vol. 119, pp. 383–3831; (6) Cloke et al., "Zirconium Complexes incorporating the New Tridentate Diamide Ligand [(Me$_3$Si)N{CH$_2$CH$_2$N(SiMe$_3$)}$_2$]$^{2-}$(L); the Crystal Structure of [Zr(BH$_4$)$_2$L] and [ZrCl{CH(SiMe$_3$)$_2$}L]", J. Chem. Soc. Dalton Trans, pp. 25–30, 1995; (7) Clark et al., "Titanium (IV) complexes incorporating the aminodiamide ligand [(SiMe$_3$)N{CH$_2$CH$_2$N (SiMe$_3$)}$_2$]$^{2-}$(L); the X-ray crystal structure of [TiMe$_2$(L)] and [TiCl{CH(SiMe$_3$)$_2$}(L)]", Journal of Organometallic Chemistry, Vol 50, pp. 333–340, 1995; (8) Scollard et al., "Living Polymerization of alpha-olefins by Chelating Diamide Complexes of Titanium", J. Am. Chem. Soc., Vol 118, No. 41, pp. 10008–10009, 1996; and (9) Guerin et al., "Conformationally Rigid Diamide Complexes: Synthesis and Structure of Titanium (IV) Alkyl Derivatives", Organometallics, Vol 15, No. 24, pp. 5085–5089, 1996.

Furthermore, U.S. Pat. No. 5,576,460 describes a preparation of arylamine ligands and U.S. Pat. No. 5,889,128 discloses a process for the living polymerization of olefins using initiators having a metal atom and a ligand having two group 15 atoms and a group 16 atom or three group 15 atoms. EP 893 454 A1 also describes preferably titanium transition metal amide compounds. In addition, U.S. Pat. No. 5,318,935 discusses amido transition metal compounds and catalyst systems especially for the producing isotactic polypropylene. Polymerization catalysts containing bidentate and tridentate ligands are further discussed in U.S. Pat. No. 5,506,184.

Additionally, in U.S. application Ser. No. 09/460,179, filed Dec. 10, 1999 describes Group 15 catalyst compounds used in combination with an aluminum containing ionizing activator. U.S. application Ser. No. 09/425,390 filed Oct. 22, 1999 describes the use of a Group 15 catalyst compound in combination with a bulky ligand metallocene catalyst compound. While these Group 15 containing catalyst compounds are useful, a need exits in the industry to improve the commercial viability of these new catalyst developments.

There are a variety of techniques discussed for preparing a supported activator and to its use in a catalyst system for polymerizing olefin(s), mostly where the catalyst compounds are bulky ligand metallocene catalyst compounds. The following non-limiting examples of patent publications discussing supported activators, which are all filly incorporated herein by reference, include: U.S. Pat. No. 5,728,855 directed to the forming a supported oligomeric alkylaluminoxane formed by treating a trialkylaluminum with carbon dioxide prior to hydrolysis; U.S. Pat. Nos. 5,831,109 and 5,777,143 discusses a supported methylalumoxane made using a non-hydrolytic process; U.S. Pat. No. 5,731,451 relates to a process for making a supported alumoxane by oxygenation with a trialkylsiloxy moiety; U.S. Pat. No. 5,856,255 discusses forming a supported auxiliary catalyst (alumoxane or organoboron compound) at elevated temperatures and pressures; U.S. Pat. No. 5,739,368 discusses a process of heat treating alumoxane and placing it on a support; EP-A-0 545 152 relates to adding a metallocene to a supported alumoxane and adding more methylalumoxane; U.S. Pat. Nos. 5,756,416 and 6,028,151 discuss a catalyst composition of a alumoxane impregnated support and a metallocene and a bulky aluminum alkyl and methylalumoxane; EP-B 1-0 662 979 discusses the use of a metallocene with a catalyst support of silica reacted with alumoxane; PCT WO 96/16092 relates to a heated support treated with alumoxane and washing to remove unfixed alumoxane; U.S. Pat. Nos. 4,912,075, 4,937,301, 5,008,228, 5,086,025, 5,147,949, 4,871,705, 5,229,478, 4,935,397, 4,937,217 and 5,057,475, and PCT WO 94/26793 all directed to adding a metallocene to a supported activator; U.S. Pat. No. 5,902,766 relates to a supported activator having a specified distribution of alumoxane on the silica particles; U.S. Pat. No. 5,468,702 relates to aging a supported activator and adding a metallocene; U.S. Pat. No. 5,968,864 discusses treating a solid with alumoxane and introducing a metallocene; EP 0 747 430 A1 relates to a process using a metallocene on a supported methylalumoxane and trimethylaluminum; EP 0 969 019 A1 discusses the use of a metallocene and a supported activator; EP-B2-0 170 059 relates to a polymerization process using a metallocene and a organoaluminuim compound, which is formed by reacting aluminum trialkyl with a water containing support; U.S. Pat. No. 5,212,232 discusses the use of a supported alumoxane and a metallocene for producing styrene based polymers; U.S. Pat. No. 5,026,797 discusses a polymerization process using a solid component of a zirconium compound and a water-insoluble porous inorganic oxide preliminarily treated with alumoxane; U.S. Pat. No. 5,910,463 relates to a process for preparing a catalyst support by combining a dehydrated support material, an alumoxane and a polyfunctional organic crosslinker, U.S. Pat. Nos. 5,332,706, 5,473,028, 5,602,067 and 5,420,220 discusses a process for making a supported activator where the volume of alumoxane solution is less than the pore volume of the support material; WO 98/02246 discusses silica treated with a solution containing a source of aluminum and a metallocene; WO 99/03580 relates to the use of a supported alumoxane and a metallocene; EP-A1-0 953 581 discloses a heterogeneous catalytic system of a supported alumoxane and a metallocene; U.S. Pat. No. 5,015,749 discusses a process for preparing a polyhydrocarbyl-alumoxane using a porous organic or inorganic imbiber material; U.S. Pat. Nos. 5,446,001 and 5,534,474 relates to a process for preparing one or more alkyla-luminoxanes immobilized on a solid, particulate inert support; and EP-A1-0 819 706 relates to a process for preparing a solid silica treated with alumoxane. Also, the following articles, also fully incorporated herein by reference for purposes of disclosing useful supported activators and methods for their preparation, include: W. Kaminsky, et al., "Polymerization of Styrene with Supported Half-Sandwich Complexes", Journal of Polymer Science Vol. 37, 2959–2968 (1999) describes a process of adsorbing a methylalumoxane to a support followed by the adsorption of a metallocene; Junting Xu, et al. "Characterization of isotactic polypropylene prepared with dimethylsilyl bis(1-indenyl) zirconium dichloride supported on methylaluminoxane pretreated silica", European Polymer Jourmal 35 (1999) 1289–1294, discusses the use of silica treated with methylalumoxane and a metallocene; Stephen O'Brien, et al., "EXAFS analysis of a chiral alkene polymerization catalyst incorporated in the mesoporous silicate MCM-41" Chem. Commun. 1905–1906 (1997) discloses an immobilized alumoxane on a modified mesoporous silica; and F. Bonini, et al., "Propylene Polymerization through Supported Metallocene/MAO Catalysts: Kinetic Analysis and Modeling" Journal of Polymer Science, Vol. 33 2393–2402 (1995) discusses using a methylalumoxane supported silica with a metallocene.

Also, combination of activators have described in for example, U.S. Pat. Nos. 5,153,157 and 5,453,410, European publication EP-B1 0 573 120, and PCT publications WO 94/07928 and WO 95/14044. These documents all discuss the use of an alumoxane and an ionizing activator with a bulky ligand metallocene catalyst compound.

While all these methods have been described in the art, a need for an improved method for preparing a catalyst composition utilizing Group 15 containing catalyst compounds has been discovered.

SUMMARY OF THE INVENTION

This invention provides for a catalyst system and for its use in a polymerizing process.

In one embodiment, the invention relates to a method for making a catalyst composition comprising the steps of: (a) forming a supported activator; (b) introducing a Group 15 containing catalyst compound; and (c) introducing an ionizing activator.

In another embodiment the invention is directed to a catalyst composition of a supported activator, a Group 15 containing compound and an ionizing activator, preferably where the ionizing activator is a Group 13 containing ionizing activator.

In an embodiment, the invention is directed to forming a catalyst composition of a Group 15 containing bidentate or tridentate ligated transition metal catalyst compound, a supported activator comprising the product of combining a support material and an activator, and an ionizing activator, and to its use in the polymerization of olefin(s). In the most preferred embodiment, the activator is an aluminum containing compound and the ionizing activator is a boron containing compound.

In another embodiment, the invention is directed to a catalyst composition of a catalyst compound having a transition metal bound to at least one leaving group and also bound to at least two Group 15 atoms, at least one of which is also bound to a Group 15 or 16 atom through another group, a supported activator, preferably a supported alumoxane, and an ionizing activator, and to its use in the polymerization of olefin(s).

In another embodiment, the invention is directed to a process for polymerizing olefin(s), particularly in a gas phase or slurry phase process, utilizing any one of the catalyst compositions discussed above.

DETAILED DESCRIPTION OF THE INVENTION

Introduction

It has been found that the catalyst composition of the invention which includes a supported activator, at least one Group 15 containing transition metal catalyst compound, and an ionizing activator having higher commercially acceptable activities. Also, the catalyst composition of the invention has a higher comonomer incorporation rate when utilized in the polymerization of one or more olefin(s). Furthermore, the catalyst composition of the invention, in one particular embodiment, is useful in a slurry form, thus not requiring the need to remove all liquids involved in forming a traditional supported catalyst system.

Group 15 Containing Metal Catalyst Compound and Catalyst Systems

In one embodiment, the metal based catalyst compounds utilized in the catalyst composition of the invention are Group 15 bidentate or tridentate ligated transition metal compound having at least one substituted hydrocarbon group, the preferred Group 15 elements are nitrogen and/or phosphorous, most preferably nitrogen, and the preferred leaving group is a substituted alkyl group having greater than 6 carbon atoms, preferably the alkyl substituted with an aryl group.

The Group 15 containing metal catalyst compounds of the invention generally include a transition metal atom bound to at least one substituted hydrocarbon leaving group and also bound to at least two Group 15 atoms, at least one of which is also bound to a Group 15 or 16 atom through another group.

In one preferred embodiment, at least one of the Group 15 atoms is also bound to a Group 15 or 16 atom through another group, which may be a hydrocarbon group, preferably a hydrocarbon group having 1 to 20 carbon atoms, a heteroatom containing group, preferably silicon, germanium, tin, lead, or phosphorus. In this embodiment, it is further preferred that the Group 15 or 16 atom be bound to nothing or a hydrogen, a Group 14 atom containing group, a halogen, or a heteroatom containing group. Additionally in these embodiment, it is preferred that each of the two Group 15 atoms are also bound to a cyclic group that may optionally be bound to hydrogen, a halogen, a heteroatom or a hydrocarbyl group, or a heteroatom containing group.

In an embodiment of the invention, the Group 15 containing metal compound of the invention is represented by the formulae:

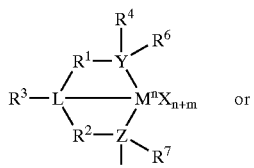

Formula (I)

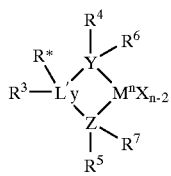

Formula (II)

wherein M is a metal, preferably a transition metal, more preferably a Group 4,5 or 6 metal, even more preferably a Group 4 metal, and most preferably hafnium or zirconium; each X is independently a leaving group, preferably, an anionic leaving group, and more preferably hydrogen, a hydrocarbyl group, a heteroatom, and most preferably an alkyl. In a most preferred embodiment, at least one X is a substituted hydrocarbon group, preferably a substituted alkyl group having more than 6 carbon atoms, more preferably an aryl substituted alkyl group and most preferably a benzyl group.

y is 0 or 1 (when y is 0 group L' is absent);

n is the oxidation state of M, preferably +2, +3, +4 or +5 and more preferably +4;

m is the formal charge of the YZL or the YZL' ligand, preferably 0, −1, −2 or −3, and more preferably −2;

L is a Group 15 or 16 element, preferably nitrogen;

L' is a Group 15 or 16 element or Group 14 containing group, preferably carbon, silicon or germanium;

Y is a Group 15 element, preferably nitrogen or phosphorus, and more preferably nitrogen;

Z is a Group 15 element, preferably nitrogen or phosphorus, and more preferably nitrogen;

$R^1$ and $R^2$ are independently a $C_1$ to $C_{20}$ hydrocarbon group, a heteroatom containing group having up to twenty carbon atoms, silicon, germanium, tin, lead, or phosphorus, preferably a $C_2$ to $C_{20}$ alkyl, aryl or arylalkyl group, more preferably a linear, branched or cyclic $C_2$ to $C_{20}$ alkyl group, most preferably a $C_2$ to $C_6$ hydrocarbon group;

$R^3$ is absent or a hydrocarbon group, hydrogen, a halogen, a heteroatom containing group, preferably a linear, cyclic or branched alkyl group having 1 to 20 carbon atoms, more preferably $R^3$ is absent, hydrogen or an alkyl group, and most preferably hydrogen;

$R^4$ and $R^5$ are independently an alkyl group, an aryl group, substituted aryl group, a cyclic alkyl group, a substituted cyclic alkyl group, a cyclic arylalkyl group, a substituted cyclic arylalkyl group or multiple ring system, preferably having up to 20 carbon atoms, more preferably between 3 and 10 carbon atoms, and even more preferably a $C_1$ to $C_{20}$ hydrocarbon group, a $C_1$ to $C_{20}$ aryl group or a $C_1$ to $C_{20}$ arylalkyl group, or a heteroatom containing group, for example $PR_3$, where R is an alkyl group;

$R^1$ and $R^2$ may be interconnected to each other, and/or $R^4$ and $R^5$ may be interconnected to each other;

$R^6$ and $R^7$ are independently absent, or hydrogen, an alkyl group, halogen, heteroatom or a hydrocarbyl group, preferably a linear, cyclic or branched alkyl group having 1 to 20 carbon atoms, more preferably absent; and R* is absent, or is hydrogen, a Group 14 atom containing group, a halogen, a heteroatom containing group.

By "formal charge of the YZL or YZL' ligand", it is meant the charge of the entire ligand absent the metal and the leaving groups X.

By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups.

An alkyl group may be a linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. An arylalkyl group is defined to be a substituted aryl group.

In a preferred embodiment $R^4$ and $R^5$ are independently a group represented by the following formula:

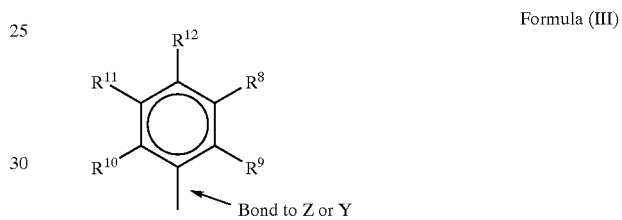

Formula (III)

wherein $R^8$ to $R^{12}$ are each independently hydrogen, a $C_1$ to $C_{20}$ alkyl group, a halide, a heteroatom, a heteroatom containing group containing up to 40 carbon atoms, preferably a $C_1$ to $C_{20}$ linear or branched alkyl group, preferably a methyl, ethyl, propyl or butyl group, any two R groups may form a cyclic group and/or a heterocyclic group. The cyclic groups may be aromatic. In a preferred embodiment $R^9$, $R^{10}$ and $R^{12}$ are independently a methyl, ethyl, propyl or butyl group (including all isomers), in a preferred embodiment $R^9$, $R^{10}$ and $R^{12}$ are methyl groups, and $R^8$ and $R^{11}$ are hydrogen.

In a particularly preferred embodiment $R^4$ and $R^5$ are both a group represented by the following formula:

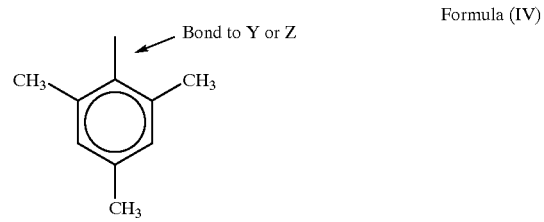

Formula (IV)

In this embodiment, M is hafnium or zirconium; each of L, Y, and Z is nitrogen; each of $R^1$ and $R^2$ is a hydrocarbyl group, preferably —$CH_2$—$CH_2$—; $R^3$ is hydrogen; and $R^6$ and $R^7$ are absent.

The Group 15 containing metal catalyst compounds utilized in the catalyst composition of the invention are prepared by methods known in the art, such as those disclosed in EP 0 893 454 A1, U.S. Pat. No. 5,889,128 and the references cited in U.S. Pat. No. 5,889,128 which are all herein incorporated by reference. U.S. application Ser. No.

09/312,878, filed May 17, 1999, discloses a gas or slurry phase polymerization process using a supported bisamide catalyst, which is also incorporated herein by reference. A preferred direct synthesis of these compounds comprises reacting the neutral ligand, (see for example YZL or YZL' of Formula I or II) with $MX_n$, n is the oxidation state of the metal, each X is an anionic group, such as halide, in a non-coordinating or weakly coordinating solvent, such as ether, toluene, xylene, benzene, methylene chloride, and/or hexane or other solvent having a boiling point above 60° C., at about 20° C. to about 150° C. (preferably 20° C. to 100° C.), preferably for 24 hours or more, then treating the mixture with an excess (such as four or more equivalents) of an alkylating agent, such as methyl magnesium bromide in ether. The magnesium salts are removed by filtration, and the metal complex isolated by standard techniques.

In one embodiment the Group 15 containing metal catalyst compound is prepared by a method comprising reacting a neutral ligand, (see for example YZL or YZL' of formula 1 or 2) with a compound represented by the formula $MX_n$ (where n is the oxidation state of M, M is a transition metal, and each X is an anionic leaving group) in a non-coordinating or weakly coordinating solvent, at about 20° C. or above, preferably at about 20° C. to about 100° C., then treating the mixture with an excess of an alkylating agent, then recovering the metal complex. In a preferred embodiment the solvent has a boiling point above 60° C., such as toluene, xylene, benzene, and/or hexane. In another embodiment the solvent comprises ether and/or methylene chloride, either being preferable.

In one embodiment, two or more Group 15 containing compounds as discussed above are used in combination with a supported activator and an ionizing activator.

In yet another embodiment, the Group 15 containing catalyst compounds of the invention are combined with one or a combination of the following catalyst compounds: (1) those catalyst compounds having bidentate ligands containing pyridine or quinoline moieties, such as those described in U.S. application Ser. No. 09/103,620 filed Jun. 23, 1998, or those bulky ligands described in PCT publications WO 99/01481 and WO 98/42664, which are fully incorporated herein by reference; (2) those catalyst compounds of $Ni^{2+}$ and $Pd^{2+}$ described in the articles Johnson, et al., "New Pd(II)- and Ni(II)-Based Catalysts for Polymerization of Ethylene and a-Olefins", J. Am. Chem. Soc. 1995, 117, 6414–6415 and Johnson, et al., "Copolymerization of Ethylene and Propylene with Functionalized Vinyl Monomers by Palladium(II) Catalysts", J. Am. Chem. Soc., 1996, 118, 267–268, and WO 96/23010 published Aug. 1, 1996, WO 99/02472, U.S. Pat. Nos. 5,852,145, 5,866,663 and 5,880, 241, which are all herein fully incorporated by reference;(3) those catalyst compounds of diimine based ligands of Group 8 to 10 metal compounds as disclosed in PCT publications WO 96/23010, WO 97/48735 and WO 98/40374 and Gibson, et. al., Chem. Comm., pp. 849–850 (1998), all of which are herein incorporated by reference; (4) those catalyst compounds that are traditional metallocene catalysts as described in U.S. Pat. Nos. 5,324,800, 5,064,802, 5,145,819, 5,149,819, 5,243,001, 5,239,022, 5,276,208, 5,296,434, 5,057,475, 5,096,867, 5,055,438, 5,198,401, 5,227,440, 5,264,405, 5,321,106, 5,329,031, 5,304,614, 5,677,401, 5,723,398, 5,753,578, 5,854,363, 5,856,547 5,858,903, 5,859,158, 5,900,517, 5,939,503 and 5,962,718 and PCT publications WO 93/08221, WO 93/08199, WO 92/00333, WO 94/07928, WO 91/04257, WO 94/03506, WO96/00244, WO 97/15602, WO 99/20637, WO 95/07140, WO 98/11144, WO 98/41530, WO 98/41529, WO 98/46650, WO 99/02540 and WO 99/14221 and European publications EP-A-0 578 838, EP-A-0 638 595, EP-B-0 513 380, EP-A1-0 816 372, EP-A2-0 839 834, EP-A-0 420 436, EP-B1-0 632 819, EP-B1-0 739 361, EP-B1-0 748 821 and EP-B1-0 757 996, all of which are herein fully incorporated by reference; and (5) those traditional Ziegler-Natta catalysts and Phillips-type chromium catalyst well known in the art for example as discussed in U.S. Pat. Nos. 4,115,639, 4,077,904 4,482,687, 4,564,605, 4,721,763, 4,879,359 and 4,960,741 all of which are herein fully incorporated by reference.

Activators

For the purposes of this patent specification and appended claims, the term "activator" is defined to be any compound or component or method which can activate any of the catalyst compounds or combinations thereof of the invention for the polymerization of olefin(s).

Supported Activators

Many of the supported activators of the invention are described in the various patents and publications in the background of this patent specification, all of which are herein fully incorporated by reference. Any of the methods discussed are useful for producing the supported activator component of the invention. In one embodiment, alumoxanes as activators are used in the supported activator of the invention. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. A variety of methods for preparing alumoxanes and modified alumoxanes are described in U.S. Pat. Nos. 4,665,208, 4,952,540, 5,091,352, 5,206,199, 5,204,419, 4,874,734, 4,924,018, 4,908,463, 4,968,827, 5,041,584, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publication WO 94/10180. Other alumoxanes include siloxy alumoxanes as described in EP-B1-0 621 279 and U.S. Pat. No. 6,060,418, and chemically functionalized carboxylate-alumoxane described in WO 00/09578, which are herein incorporated by reference.

Other activators useful in forming the supported activator of the invention are aluminum alkyl compounds, such as trialkylaluminums and alkyl aluminum chlorides. Examples of these activators include trimethylaluminum, triethylaluminum, triisobutylaluminum, tri-n-hexylaluminum, tri-n-octylaluminum and the like.

The above-described activators may be combined with one or more support materials also described above using one or more support methods well known in the art. For example, in a most preferred embodiment, an activator is deposited on, contacted with, or incorporated within, vaporized onto, reacted with, adsorbed or absorbed in, or on, a support material.

The support material for forming the supported activator is any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred support materials include silica, alumina, silica-alumina, magnesium chloride, and mixtures thereof. Other useful support materials include magnesia, titania, zirconia, montmorillonite (EP-B1 0 511 665), hydrotalcites, and the like. Also, combinations of these support materials may be used, for example, silica-chromium, silica-alumina, silica-titania and the like.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 $\mu$m. More preferably, the surface area of the support material is in the range of from about 50 to about 500 m$^2$/g, pore volume of from about 0.5 to about 3.5 cc/g and average particle size of from about 10 to about 200 $\mu$m. Most preferably the surface area of the support material is in the range is from about 100 to about 400 m$^2$/g, pore volume from about 0.8 to about 3.0 cc/g and average particle size is from about 5 to about 100 $\mu$m. The average pore size of the carrier of the invention typically has pore size in the range of from 10 to 1000 Å, preferably 50 to about 500 Å, and most preferably 75 to about 350 Å.

The support materials may be treated chemically, for example with a fluoride compound as described in WO 00/12565, which is herein incorporated by reference. Other supported activators are described in for example WO 00/13792 that refers to supported boron containing solid acid complex.

In a preferred method of forming the supported activator the amount of liquid in which the activator is present is in an amount that is less than four times the pore volume of the support material, more preferably less than three times, even more preferably less than two times; preferred ranges being from 1.1 times to 3.5 times range and most preferably in the 1.2 to 3 times range. In an alternative embodiment, the amount of liquid in which the activator is present is from one to less than one times the pore volume of the support material utilized in forming the supported activator.

Procedures for measuring the total pore volume of a porous support are well known in the art. Details of one of these procedures is discussed in Volume 1, *Experimental Methods in Catalytic Research* (Academic Press, 1968) (specifically see pages 67–96). This preferred procedure involves the use of a classical BET apparatus for nitrogen absorption. Another method well known in the art is described in Innes, *Total Porosity and Particle Density of Fluid Catalysts By Liquid Titration*, Vol. 28, No. 3, Analytical Chemistry 332–334 (March, 1956).

In an embodiment, the supported activator is in a dried state, a solid. In another embodiment, the supported activator is in a substantially dry state or a slurry, preferably in a mineral oil slurry.

In another embodiment, two or more separately supported activators are used, or alternatively, two or more different activators on a single support are used.

Ionizing Activators

Ionizing activators of the invention, in one embodiment are those ionizing or stoichiometric activators, which are either neutral or ionic. For example ionizing activators include tri (n-butyl) ammonium tetrakis (pentafluorophenyl) boron, a trisperfluorophenyl boron metalloid precursor or a trisperfluoronaphtyl boron metalloid precursor, polyhalogenated heteroborane anions (WO 98/43983) or combination thereof, that would ionize the neutral catalyst compound. It is also within the scope of this invention to use neutral and ionic ionizing activators in combination.

Examples of neutral stoichiometric ionizing activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. More preferably, the three groups are a fluorinated hydrocarbyl group having 1 to 20 carbon atoms, preferably a fluorinated aryl group, and more preferably a pentafluoryl aryl group. Most preferably, the neutral stoichiometric activator is trisperfluorophenyl boron or trisperfluoronapthyl boron.

Ionic stoichiometric ionizing activators, in one embodiment, contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

In a preferred embodiment, the ionizing activators include a cation and an anion component, and is represented by the following formula:

$$(L'''-H)_d^+ (A^{d-}) \tag{V}$$

wherein L''' is an neutral Lewis base;

H is hydrogen;

(L'''-H)+is a Bronsted acid $A^{d-}$ is a non-coordinating anion having the charge d− d is an integer from 1 to 3.

The cation component, $(L'''-H)_d^+$ may include Bronsted acids such as protons or protonated Lewis bases or reducible Lewis acids capable of protonating or abstracting a moiety, such as an akyl or aryl, from the catalysts compound of the invention, in particular the Group 15 containing transition metal catalyst compound, resulting in a cationic transition metal species.

The activating cation $(L'''-H)_d^+$ may be a Bronsted acid, capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene and mixtures thereof. The activating cation (L'''-H)$_d^+$ may also be an abstracting moiety such as silver, carboniums, tropylium, carbeniums, ferroceniums and mixtures, preferably carboniums and ferroceniums. Most preferably (L'''-H)$_d^+$ is triphenyl carbonium.

The anion component A$^{d-}$ include those having the formula [M$^{k+}$Q$_n$]$^{d-}$ wherein k is an integer from 1 to 3; n is an integer from 2–6; n−k=d; M is an element selected from Group 13 of the Periodic Table of the Elements and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable A$^{d-}$ also include diboron compounds as disclosed in U.S. Pat. No. 5,447,895, which is fully incorporated herein by reference.

Most preferably, the ionic stoichiometric activator (L'''-H)$_d^+$(A$^{d-}$) is N,N-dimethylanilinium tetra(perfluorophenyl)borate or triphenylcarbenium tetra(perfluorophenyl)borate.

Other activators include those described in PCT publication WO 98/07515 such as tris (2,2', 2''-nonafluorobiphenyl) fluoroaluminate, which publication is fully incorporated herein by reference. WO 98/09996 incorporated herein by reference describes activating metal compounds with perchlorates, periodates and iodates including their hydrates. WO 98/30602 and WO 98/30603 incorporated by reference describe the use of lithium (2,2'-bisphenyl-ditrimethylsilicate)·4THF as an activator. EP-A2-0 103 675 describes fluorinated organic compound activators, which is herein incorporated by reference. WO 99/18135 incorporated herein by reference describes the use of organo-boron-aluminum activators. EP-B1-0 781 299 describes using a silylium salt in combination with a non-coordinating compatible anion. Other activators are described in for example, U.S. Pat. Nos. 5,849,852, 5,859,653, 5,869,723 and 6,030,917 (gallium based anion activators) and PCT WO 98/32775, WO 00/09513 (three coordinate aluminum activator) and WO 00/20115, which are all herein incorporated by reference.

Catalyst Composition

The catalyst composition of the invention is formed in various ways. In one embodiment, a supported activator is combined with a Group 15 transition metal compound and an ionizing activator, preferably in mineral oil.

In a preferred embodiment, the resulting mixture of the combination of the supported activator, Group 15 transition metal catalyst compound and the ionizing activator is stirred for a period of time and at a specified temperature. In one embodiment, the mixing time is in the range of from 1 minute to several days, preferably about one hour to about a day, more preferably from about 2 hours to about 20 hours, and most preferably from about 5 hours to about 16 hours. The period of contacting refers to the mixing time only.

The mixing temperature ranges from −60° C. to about 200° C., preferably from 0° C. to about 100° C., more preferably from about 10° C. to about 60° C., still more preferably from 20° C. to about 40° C., and most preferably at room temperature.

In general the Group 15 transition metal catalyst compound and supported activator, for example in the preferred embodiment, where the supported activator is a supported aluminum compound, most preferably alumoxane, the ratio of aluminum atom to catalyst transition metal atom is about 1000:1 to about 1:1. preferably a ratio of about 300:1 to about 1:1, and more preferably about 50:1 to about 250:1, and most preferably from 100:1 to 125:1.

In another embodiment, the ionizing activator compound is utilized in a quantity that provides a mole ratio of the ionizing activator to the catalyst transition metal atom of from about 0.01 to 1.0, preferably from about 0.1 to about 0.9, more preferably from 0.2 to about 0.8 and most preferably from about 0.3 to 0.7.

In another embodiment the combined amount in weight percent of the supported activator to the Group 15 containing transition metal compound and the ionizing compound are in the range of from 99.9 weight percent to 50 weight percent, preferably from about 99.8 weight percent to about 60 weight percent, more preferably from about 99.7 weight percent to about 70 weight percent, and most preferably from about 99.6 weight percent to about 80 weight percent.

In other embodiments of the invention the supported activator is in a dry or substantially dried state, or in a solution, when contacted with the Group 15 containing transition metal catalyst and the ionizing activator. In this embodiment, the resulting catalyst composition is used in a dry or substantially dry state, or as a slurry, in preferably a mineral oil. Also, the dried catalyst composition of the invention can be reslurried in a liquid such as mineral oil, toluene, or any the hydrocarbon prior to its introduction into a polymerization reactor.

Furthermore, it is contemplated that the supported activator, Group 15 containing catalyst compound and the ionizing activator can be used in the same solvents or different solvents. For example, the catalyst compound can be in toluene, the ionizing activator in isopentane and the supported activator in mineral oil, or any combination of solvents. In the most preferred embodiment, the solvent is the same, and is most preferably a mineral oil.

Antistatic agents or surface modifiers may be used in combination with the supported activator, Group 15 containing catalyst compound and ionizing activator, see for example those agents and modifiers described in PCT publication WO 96/11960, which is herein fully incorporated by reference. Also, a carboxylic acid salt of a metal ester, for example aluminum carboxylates such as aluminum mono, di- and tri-stearates, aluminum octoates, oleates and cyclohexylbutyrates, as described in U.S. application Ser. No. 09/113,216, filed Jul. 10, 1998 may be used in combination with a supported activator, Group 15 containing catalyst compound and ionizing activator.

In one embodiment of the invention, olefin(s), preferably $C_2$ to $C_{30}$ olefin(s) or alpha-olefin(s), preferably ethylene or propylene or combinations thereof are prepolymerized in the presence of the supported activator, Group 15 containing catalyst compound and ionizing activator combination prior to the main polymerization. The prepolymerization can be carried out batchwise or continuously in gas, solution or slurry phase including at elevated pressures. The prepolymerization can take place with any olefin monomer or combination and/or in the presence of any molecular weight controlling agent such as hydrogen. For examples of prepolymerization procedures, see U.S. Pat. Nos. 4,748,221, 4,789,359, 4,923,833, 4,921,825, 5,283,278 and 5,705,578 and European Publication EP-B 1-0 279 863 and PCT Publication WO 97/44371, and all of which are herein fully incorporated by reference.

Polymerization Process

The catalyst composition of the invention described above are suitable for use in any polymerization process over a wide range of temperatures and pressures. The temperatures may be in the range of from −60° C. to about 280° C., preferably from 50° C. to about 200° C., and the pressures employed may be in the range from 1 atmosphere to about 500 atmospheres or higher.

Polymerization processes include solution, gas phase, slurry phase and a high pressure process or a combination thereof. Particularly preferred is a gas phase or slurry phase polymerization of one or more olefin(s) at least one of which is ethylene or propylene.

In one embodiment, the process of this invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, butene-1, pentene-1, 4-methyl-pentene-1, hexene-1, octene-1 and decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In the most preferred embodiment of the process of the invention, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In one embodiment, the invention is directed to a polymerization process, particularly a gas phase or slurry phase process, for polymerizing propylene alone or with one or more other monomers including ethylene, and/or other olefins having from 4 to 12 carbon atoms. Polypropylene polymers may be produced using the particularly bridged bulky ligands and metal compounds as described in U.S. Pat. Nos. 5,296,434 and 5,278,264, both of which are herein incorporated by reference.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.)

The reactor pressure in a gas phase process may vary from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

Other gas phase processes contemplated by the process of the invention include series or multistage polymerization processes. Also gas phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-0 634 421 all of which are herein fully incorporated by reference.

In a preferred embodiment, the reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A preferred polymerization technique of the invention is referred to as a particle form polymerization, or a slurry process where the temperature is kept below the temperature at which the polymer goes into solution. Such technique is well known in the art and described in for instance U.S. Pat. No. 3,248,179, which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In an embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998 and 5,589,555, which are fully incorporated herein by reference.

A preferred process of the invention is where the process, preferably a slurry or gas phase process is operated in the presence of the catalyst composition of the invention and in the absence of or essentially free of any scavengers, such as triethylaluminum, trimethylaluminum, tri-isobutylaluminum and tri-n-hexylaluminum and diethyl aluminum chloride, dibutyl zinc and the like. This preferred process is described in PCT publication WO 96/08520 and U.S. Pat. Nos. 5,712,352 and 5,763,543, which are herein fully incorporated by reference.

Polymer Products

The polymers produced by the process of the invention can be used in a wide variety of products and end-use applications. The polymers produced by the process of the invention include linear low-density polyethylene, elastomers, plastomers, high-density polyethylenes, low-density polyethylenes, polypropylene and polypropylene copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. Density is measured in accordance with ASTM-D-1238.

The polymers produced by the process of the invention typically have a molecular weight distribution, a weight average molecular weight to number average molecular weight ($M_w/M_n$) of greater than 1.5 to about 15, particularly greater than 2 to about 10, more preferably greater than about 2.2 to less than about 8, and most preferably from 2.5 to 8.

Also, the polymers of the invention typically have a narrow composition distribution as measured by Composition Distribution Breadth Index (CDBI). Further details of determining the CDBI of a copolymer are known to those skilled in the art. See, for example, PCT Patent Application WO 93/03093, published Feb. 18, 1993, which is fully incorporated herein by reference.

The bulky ligand metallocene catalyzed polymers of the invention in one embodiment have CDBI's generally in the range of greater than 50% to 100%, preferably 99%, preferably in the range of 55% to 85%, and more preferably 60% to 80%, even more preferably greater than 60%, still even more preferably greater than 65%.

In another embodiment, polymers produced using a bulky ligand metallocene catalyst system of the invention have a CDBI less than 50%, more preferably less than 40%, and most preferably less than 30%.

The polymers of the present invention in one embodiment have a melt index (MI) or ($I_2$) as measured by ASTM-D-1238-E in the range from 0.01 dg/min to 1000 dg/rin, more preferably from about 0.01 dg/min to about 100 dg/min, even more preferably from about 0.1 dg/min to about 50 dg/min, and most preferably from about 0.1 dg/min to about 10 dg/min.

The polymers of the invention in an embodiment have a melt index ratio ($I_{21}/I_2$) ($I_{21}$ is measured by ASTM-D-1238-F) of from 10 to less than 25, more preferably from about 15 to less than 25.

The polymers of the invention in a preferred embodiment have a melt index ratio ($I_{21}/I_2$) ($I_{21}$ is measured by ASTM-D-1238-F) of from preferably greater than 25, more preferably greater than 30, even more preferably greater that 40, still even more preferably greater than 50 and most preferably greater than 65. In an embodiment, the polymer of the invention may have a narrow molecular weight distribution and a broad composition distribution or vice-versa, and may be those polymers described in U.S. Pat. No. 5,798,427 incorporated herein by reference.

In yet another embodiment, propylene based polymers are produced in the process of the invention. These polymers include atactic polypropylene, isotactic polypropylene, hemi-isotactic and syndiotactic polypropylene. Other propylene polymers include propylene block or impact copolymers. Propylene polymers of these types are well known in the art see for example U.S. Pat. Nos. 4,794,096, 3,248,455, 4,376,851, 5,036,034 and 5,459,117, all of which are herein incorporated by reference.

The polymers of the invention may be blended and/or coextruded with any other polymer. Non-limiting examples of other polymers include linear low density polyethylenes produced via conventional Ziegler-Natta and/or bulky ligand metallocene catalysis, elastomers, plastomers, high pressure low density polyethylene, high density polyethylenes, polypropylenes and the like.

Polymers produced by the process of the invention and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc.

EXAMPLES

In order to provide a better understanding of the present invention including representative advantages thereof, the following examples are offered.

Activity values in Table 1 are normalized values based upon grams of polymer produced per mmol of transition metal in the catalyst per hour per 100 psi (690 kPa) of ethylene polymerization pressure. MI is Melt Index, and was reported as grams per 10 minutes per ASTM D-1238, Condition E. FI is Flow Index, and was measured 10 times the weight used in the melt index above per ASTM D-1238, Condition F. MFR is Melt Flow Ratio, and is the ratio of FI:MI.

MAO is methylalumoxane in toluene (30 wt %), available from Albemarle Corporation, Baton Rogue, La.

Kaydol, a white mineral oil, was purchased from Witco Corporation, Memphis, Term., and was purified by first degassed with nitrogen for 1 hour, followed by heating at 80° C. under vacuum for 10 hours.

BBF is butyl branch frequency of hexene-1/ethylene copolymer as was measures on a Bruker AC 300 NMR spectrometer. All $C^{13}$ NMR experiments are done under Nuclear Overhouser Effect (NOE) conditions using a 30° pulse width and a repetition time of five (5) seconds. BBF are calculated in number of branches per 1000 backbone carbon atoms using standard assignments as is well known in the art.

BF-20 is dimethylanilinium tetrakis(pentaflurophenyl) borate and is available from Boulder Scientific Company, Mead, Colo.

Example 1
Preparation of Supported Activator

A toluene solution of methylalumoxane (MAO) was prepared by mixing 960 g of 30 wt % MAO, (MAO was purchased from Albemarle Corporation, Baton Rogue, La.), in 2.7 liter of dry, degassed toluene. This solution was stirred at ambient temperature while 850 g of silica gel (Davison 955, dehydrated at 600° C. available from W. R. Grace, Davison Division, Baltimore, Md.) was added. The resulting slurry was stirred at ambient temperature for 1 hour and the solvent was removed under reduced pressure with a stream of nitrogen at 85° C. The drying is continued until the material temperature has been constant for 2 hours. The resulting free-flowing white powder has an aluminum loading of 4.3 mmol Al per gram of solid.

The following are represented examples of forming the Group 15 containing transition metal catalyst compound of the invention. Furthermore, the two catalyst compounds used in the polymerization below are available from Albemarle Corporation, Baton Rouge, La.

Example 2
Preparation of [(2,4,6-Me$_3$C$_6$H$_2$)NHCH$_2$CH$_2$]$_2$NH (Ligand)

A 2 L one-armed Schlenk flask was charged with a magnetic stir bar, diethylenetriamine (23.450 g, 0.227 mol), mesityl bromide (90.51 g, 0.455 mol), tris(dibenzylideneacetone)dipalladium (1.041 g, 1.14 mmol), racemic-2,2'-bis(diphenylphosphino)-1,1'-binaphthyl (2.123 g, 3.41 mmol), sodium tert-butoxide (65.535 g, 0.682 mol), and toluene (800 mL). The reaction mixture was heated to 95° C. and stirred. After 4 days the reaction was complete, as judged by proton NMR spectroscopy. All solvent was removed under vacuum and the residues dissolved in diethyl ether (1 L). The ether was washed three times with water (1 L) and saturated aqueous NaCl (500 mL) and dried over magnesium sulfate. Removal of the ether in vacuo yielded a red oil which was dried at 70° C. for 12 h under vacuum (yield: 71.10 g, 92%). $^1$H NMR δ 6.83 (s, 4), 3.39 (br s, 2), 2.86 (t, 4), 2.49 (t, 4), 2.27 (s, 12), 2.21 (s, 6), 0.68 (br s, 1). $^{13}$C NMR δ 143.74, 131.35, 129.83, 129.55, 50.17, 48.56, 20.70, 18.51.

Example 2A
Preparation of {[(2,4,6-Me$_3$C$_6$H$_2$)NCH$_2$CH$_2$]$_2$NH}Hf(CH$_2$Ph)$_2$ (Hf-HN3)

A 250 mL round bottom flask was charged with a magnetic stir bar, tetrabenzyl hafnium (4.063 g, 7.482 mmol), and 150 mL of toluene under dry, oxygen-free nitrogen. Solid triamine ligand above (2.545 g, 7.495 mmol) was added with stirring over 1 minute (the desired compound precipitates). The volume of the slurry was reduced to 30 mL and 120 mL of pentane added with stirring. The solid pale yellow product was collected by filtration and dried under vacuum (4.562 g, 87% yield). $^1$H NMR (C$_6$D$_6$) δ 7.21–6.79 (m, 12), 6.16 (d, 2), 3.39 (m, 2), 3.14 (m, 2), 2.65 (s, 6), 2.40 (s, 6), 2.35 (m, 2), 2.23 (m, 2), 2.19 (s, 6) 1.60 (s, 2), 1.26 (s, 2), NH obscured.

Example 2B
Preparation of {[(2,4,6-Me$_3$C$_6$H$_2$)NCH$_2$CH$_2$]$_2$NH}Zr(CH$_2$Ph)$_2$(Zr-HN3)

A 500 mL round bottom flask was charged with a magnetic stir bar, tetrabenzyl zirconium (41.729 g, 91.56 mmol), and 300 mL of toluene under dry, oxygen-free nitrogen. Solid triamine ligand above (32.773 g, 96.52 mmol) was added with stirring over 1 minute (the desired compound precipitates). The volume of the slurry was reduced to 100 mL and 300 mL of pentane added with stirring. The solid yellow-orange product was collected by filtration and dried under vacuum (44.811 g, 80% yield). $^1$H NMR (C$_6$D$_6$) δ 7.22–6.81 (m, 12), 5.90 (d, 2), 3.38 (m, 2), 3.11 (m, 2), 3.01 (m, 1), 2.49 (m, 4), 2.43 (s, 6), 2.41 (s, 6), 2.18 (s, 6), 1.89 (s, 2), 0.96 (s, 2).

For purposes of the Table below Catalyst Compound A is Bis(2,4,6-trimethylphenyl amido ethyl) amine hafnium dibenzyl and Catalyst Compound B is Bis(2,4,6-trimethylphenyl amido ethyl)anine zirconium dibenzyl.

Example 3
Preparation of Catalyst System I

To a Kaydol oil solution of bisamide hafnium compound (Catalyst Compound A, 0.032 g, 0.0459 mmol in 8 g of Kaydol oil) were added to the supported activator prepared in Example 1 above (1.35 g). The resulting slurry, slurried catalyst system, was then stirred for 16 hours at room temperature before being used for polymerization.

Example 4
Preparation of Catalyst System II

To a Kaydol oil solution of bisamide zirconium compound (Catalyst Compound B, 0.025 g, 0.0410 mmol in 15 g of Kaydol oil) were added to the supported activator prepared in Example 1 above (1.35 g). The resulting slurry, slurried catalyst system, was then stirred for 16 hours at room temperature before being used for polymerization.

As described previously in this patent specification there a various methods for adding the ionizing activator. The following non-limiting examples exemplify the various embodiments methods of the invention.

Example 5
Methods for Introducing the Ionizing Activator

Method 1

In Method 1, the ionizing activator, the BF-20 compound described above, Catalyst Compound A or B, and the supported activator were all mixed at the same time in Kaydol oil. The resulting mixture was then stirred at room temperature for 16 hours before the catalyst composition of the invention is employed for polymerization.

Method 2

In Method 2, the Catalyst Compound A or B is mixed with the supported activator first to form Catalyst System I or II, a slurried catalyst system in Kaydol oil. Then, the ionizing activator was added directly to Catalyst System I or II. The resulting mixture, catalyst composition of the invention, was then stirred at room temperature for 16 hours before being employed for polymerization.

Method 3

In Method 3 the ionizing activator, the BF-20 compound, was mixed with a Kaydol oil slurry of the supported activator. This ionizing activator/supported activator mixture was then stirred at room temperature for 16 hour before Catalyst Compound A or B was added. The resulting mixture was then stirred for another 16 hours before being used for polymerization.

Example 6 through 16 and Comparative Examples C1–C5

Polymerization Process

In each of Examples 6 through 16 and Comparative Examples C1 through C5, polyethylene was produced in a slurry phase reactor using the catalyst composition as specified in Table 1 and the polymerization process described below. For each of Examples 6 through 16, a slurry using one of the Methods 1, 2 or 3 as described above was prepared. A sample of each of the slurried catalyst compositions prepared using Method 1, 2 or 3 was added to an 8 ounce (250 ml) bottle containing 100 ml of hexane. (In Examples 6 though 8 and 13 and 14, Catalyst System I or II is used and in Example 9 through 12 and 15 and 16, Catalyst Compounds A or B is used.) A sample of each of Catalyst System I or II was used in the Comparative Examples C1 through C5 and as identified in Table 1. Hexene-1 comonomer was added to the catalyst compositions. Anhydrous conditions were maintained. The following describes the polymerization process used for Examples 6 through 16 and Comparative Examples C1 through C5.

The slurry reactor was a 1 liter, stainless steel autoclave equipped with a mechanical agitator. The reactor was first dried by heating at 95° C. under a stream of dry nitrogen for 40 minutes. After cooling the reactor to 50° C., 500 ml of hexane was added to the reactor, followed by 0.25 ml of tri-isobutylaluminum (TIBA) in hexane (0.86 mole, used as scavenger), and the reactor component was stirred under a gentle flow of nitrogen. The catalyst composition of the invention, or the compositions in the comparative examples (where no ionizing activator was used), was then transferred to the reactor under a stream of nitrogen and the reactor was sealed. The temperature of the reactor was gradually raised to 75° C. and the reactor was pressured to 150 psi (1034 kPa) with ethylene. Heating was continued until a polymerization temperature of 85° C. was attained. Unless otherwise noted, polymerization was continued for 30 minutes, during which time ethylene was continually added to the reactor to maintain a constant pressure. At the end of 30 minutes, the reactor was vented and opened.

TABLE 1

| Example | Catalyst | Ionizing Activator[1] | Method | 1-Hexene (ml) | Activity | FI | BBF |
|---|---|---|---|---|---|---|---|
| C1 | I | — | — | 0 | 17731 | no flow | — |
| C2 | I | — | — | 20 | 16191 | 0.2 | 15.3 |
| C3 | I | — | — | 60 | 12008 | 1.6 | 42.9 |
| 6 | I | 0.54 | 2 | 0 | 26821 | no flow | — |
| 7 | I | 0.54 | 2 | 20 | 38011 | 3.1 | — |
| 8 | I | 0.54 | 2 | 60 | 55920 | 7.2 | — |
| 9 | A | 0.3 | 1 | 0 | 25037 | no flow | — |
| 10 | A | 0.3 | 1 | 20 | 40827 | 3.8 | 46.5 |
| 11 | A | 0.3 | 1 | 60 | 65413 | 20 | 86.6 |
| 12 | A | 0.59 | 3 | 60 | 66917 | 14 | — |
| C4 | II | — | — | 20 | 38391 | no flow | — |
| C5 | II | — | — | 60 | 39714 | no flow | — |
| 13 | II | 0.7 | 2 | 20 | 43534 | no flow | — |
| 14 | II | 0.7 | 2 | 60 | 54737 | no flow | — |
| 15 | B | 0.7 | 1 | 20 | 43819 | no flow | — |
| 16 | B | 0.7 | 1 | 60 | 54376 | no flow | — |

[1]The mole ratio of the ionizing activator to the metal of the Group 15 transition metal compound.

While the present invention has been described and illustrated by reference to particular embodiments, those of ordinary skill in the art will appreciate that the invention lends itself to variations not necessarily illustrated herein. For example, it is comtemplated that two or more supported activators, and two or more Group 15 catalyst compounds are used in a mixture with one or more ionizing activators. It is also contemplated that in this embodiment, that the supported activators may be the same or different. For this reason, then, reference should be made solely to the appended claims for purposes of determining the true scope of the present invention.

We claim:

1. A method for preparing a catalyst composition comprising the steps of:

(a) providing a supported alumoxane, a Group 15 containing transition metal catalyst compound, and an ionizing activator described by the formula;

$$(L'''\text{-H})_d^+ (A^{d-})$$

wherein L''' is an neutral Lewis base;

H is hydrogen;

$(L'''\text{-H})^+$ is a Bronsted acid $A^{d-}$ is a non-coordinating anion having the charge d– d is an integer from 1 to 3

(b) preparing a catalyst composition by combining the supported alumoxane compound with the Group 15 containing transition metal catalyst compound in mineral oil to form a slurried catalyst system, followed by addition of the ionizing activator and stirring for 1 to 24 hours to form the catalyst composition; or (c) preparing a catalyst composition by combining the supported alumoxane compound with mineral oil to form a slurry, followed by combining with the ionizing activator and stirring from 1 to 24 hours, followed by combining the Group 15 containing transition metal catalyst compound and stirring for 1 to 24 hours to form the catalyst composition;

characterized in that the mole ratio of the, metal of the ionizing activator to the transition metal of the Group 15 containing transition metal catalyst compound is from 0.1 to 0.9.

2. The method of claim 1 wherein the Group 15 containing transition metal compound is a Group 15 containing bidentate or tridentate ligated transition metal catalyst compound.

3. The method of claim 1 wherein the Group 15 containing transition metal compound has a transition metal bound to at least one leaving group and also bound to at least two Group 15 atoms, at least one of which is also bound to a Group 15 or 16 atom through another group.

4. The method of claim 1, wherein the Group 15 containing transition metal catalyst compound is described by the formulae:

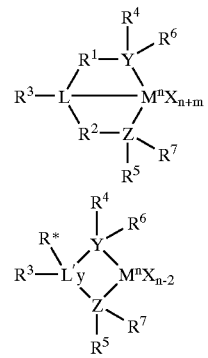

wherein M is a Group 4 metal;

each X is independently a leaving group;

n is the oxidation state of M;

m is the formal charge of the YZL or the YZL' ligand;

L is a Group 15 or 16 element;

Y is a Group 15 element;

Z is a Group 15 element;

$R^1$ and $R^2$ are independently a $C_1$ to $C_{20}$ hydrocarbon group, a heteroatom containing group having up to twenty carbon atoms, silicon, germanium, tin, lead, or phosphorus;

$R^3$ is absent or a hydrocarbon group, hydrogen, a halogen, a heteroatom containing group;

$R^4$ and $R^5$ is absent or a hydrocarbon group, hydrogen, a halogen, a heteroatom containing group;

$R^4$ and $R^5$ are independently an alkyl group, an aryl group, substituted aryl group, a cyclic alkyl group, a substituted cyclic alkyl group, a cyclic arylalkyl group, a substituted cyclic arylalkyl group or multiple ring system; wherein $R^1$ and $R^5$ may be interconnected to each other;

$R^6$ and $R^7$ are independently absent, or hydrogen, an alkyl group, halogen, heteroatom or a hydrocarbyl group; and R* is absent, or is hydrogen, a Group 14 atom, containing group, a halogen, a heteroatom containing group.

5. A process for polymerizing olefin(s) in the presence of a catalyst composition prepared by method claim 1.

6. The process of claim 5 wherein the process is a gas phase process.

7. The process of claim 5 wherein the supported activator comprises a support material and an activator.

8. The process of claim 5 wherein the catalyst composition is in a slurry state.

* * * * *